US007993381B2

(12) United States Patent
Mac et al.

(10) Patent No.: US 7,993,381 B2
(45) Date of Patent: Aug. 9, 2011

(54) METHOD AND APPARATUS FOR TREATING THE BODY

(75) Inventors: Bia Mac, San Jose, CA (US); John Iest, R. Santa Margarita, CA (US); Theresa Quach, San Jose, CA (US)

(73) Assignee: Mac Beam, Inc., San Jose, CA (US)

( * ) Notice: Subject to any disclaimer, the term of this patent is extended or adjusted under 35 U.S.C. 154(b) by 1239 days.

(21) Appl. No.: 10/814,785

(22) Filed: Apr. 1, 2004

(65) Prior Publication Data
US 2005/0228463 A1    Oct. 13, 2005

(51) Int. Cl.
*A61N 5/06* (2006.01)
(52) U.S. Cl. .............................. 607/88; 607/91; 128/907
(58) Field of Classification Search ............. 607/88–91, 607/94; 606/3–13, 16; 600/26, 27, 548; 128/907
See application file for complete search history.

(56) References Cited

U.S. PATENT DOCUMENTS

| | | | |
|---|---|---|---|
| 4,232,678 A | | 11/1980 | Skovajsa |
| 4,535,784 A | | 8/1985 | Rohlicek et al. |
| 4,835,749 A | * | 5/1989 | Welton .............................. 368/10 |
| 4,930,504 A | * | 6/1990 | Diamantopoulos et al. ..... 607/88 |
| 5,500,009 A | | 3/1996 | Mendes et al. |
| 5,755,752 A | * | 5/1998 | Segal .............................. 607/89 |
| 5,766,233 A | | 6/1998 | Thiberg |
| 5,800,479 A | | 9/1998 | Thiberg |
| 6,013,096 A | | 1/2000 | Tucek |
| 6,063,108 A | | 5/2000 | Salansky et al. |
| 6,074,411 A | * | 6/2000 | Lai et al. ......................... 607/89 |
| 6,221,095 B1 | * | 4/2001 | Van Zuylen et al. ............ 607/88 |
| 6,238,424 B1 | | 5/2001 | Thiberg |
| 6,302,900 B1 | * | 10/2001 | Riggs ................................. 607/89 |
| 6,413,267 B1 | * | 7/2002 | Dumoulin-White et al. ... 607/89 |
| 6,471,716 B1 | | 10/2002 | Pecukonis |
| 6,641,599 B2 | * | 11/2003 | Peterson et al. ................ 607/88 |
| 6,676,655 B2 | * | 1/2004 | McDaniel .......................... 606/9 |
| 6,746,473 B2 | * | 6/2004 | Shanks et al. .................... 607/89 |
| 6,866,678 B2 | * | 3/2005 | Shenderova et al. ............. 607/88 |
| 7,160,287 B1 | * | 1/2007 | Siegel ................................. 606/3 |

OTHER PUBLICATIONS

Karu, Tiina; "Photobiological Fundamentals of Low-Power Laser Therapy"; IEEE Journal of Quantum Electronics; Oct. 1987; pp. 1703-1717; vol. QE-23, No. 10.
Van Breugel, Hans et al.; "Power Density and Exposure Time of He-Ne ... "; Lasers in Surgery and Medicine; 1992; pp. 528-537; vol. 12, No. 5, Wiley-Liss Inc., U.S.
Baxter, G. David, "Therapeutic Lasers: Theory and Practice", 1997, p. 62.

* cited by examiner

*Primary Examiner* — Ahmed M Farah
(74) *Attorney, Agent, or Firm* — Shoemaker and Mattare

(57) ABSTRACT

A therapeutic method in which plural points on the body are stimulated by light of different wavelengths emitted from wands, probes or other applicators under the control of a central microprocessor. The microprocessor executes program instructions to produce light at each applicator whose intensity, frequency, duration and pulsation accord with protocols which are automatically selected depending on the portion of the body being treated. The protocols can be manually overridden by the therapist, in which case the changed parameters are stored in memory. The apparatus is particularly useful in performing traditional therapeutic methods to treat internal disorders, substance abuse, pediatric and podiatric problems and disorders of the ear, nose, throat, as well as musculoskeletal, neurological or dermatological disorders.

5 Claims, 10 Drawing Sheets

METHOD AND APPARATUS FOR TREATING THE BODY

BACKGROUND OF THE INVENTION

This invention relates to a method and apparatus for treating the body.

The apparatus of the invention uses low-intensity light to treat disorders of biological tissues, and more practically, provides a computer-controlled system including self-adhesive multiple probes and wands for applying bio-energy to the body. The invention also relates to methods of using low-intensity light for medical therapy, combining key principles from different areas of medicine.

Since the time of "the father of western medicine," Hippocrates, light and energy have been used to treat biological problems. More recently, N. R Finsen, "the father of contemporary photo-therapy", used red and ultraviolet to treat lupus vulgaris, pockmarks, and other skin diseases. However, ultraviolet must be used with caution, because it is an ionizing radiation that has the potential for damaging biomolecules.

Today, light sources are used in both the visible and the near infrared (and thus invisible) portion of the electromagnetic spectrum to provide medical therapy. Such light sources provide both coherent and polarization modes (e.g., laser diodes) and non-coherent modes (e.g., super luminous diodes).

As reported by Karu in "Photo-biological Fundamentals of Low Power Laser Therapy", IEEE Journal Quantum Electronics QE-23, 10:1703-1987, photo-biological and clinically significant reaction responses of cells have been induced by non-coherent, non-polarized, monochromatic light. Laser beams penetrate deeper into the tissue, scattering quickly and losing the coherence and polarization properties which distinguish lasers from non-laser light diodes. Electromagnetic wavelengths in the range of 400-2000 nm (both visible and invisible irradiation) provide non-ionizing radiation that does not induce mutagenic or carcinogenic effects. After over twenty years of clinical application of low-intensity light therapy, according to David Baxter (Therapeutic Lasers. P. 62, 1997), to date no serious side effects have been reported in the literature.

There are bio-energy light and heat generating apparatus combining both optical (visible) and infrared (invisible) with wavelengths ranging from 360 nm to 1,380 nm. Prior patents disclosing such devices include Nos. 4,232,678, 4,930,504, 5,500,009, 5,766,233, 5,800,479, and 4,535,784. Such devices may include a laser, laser diodes, or light emitting diodes to produce bio-energy which does not have a the potential for biological reaction in cells as does ionizing radiation in ultraviolet lights.

Devices for stimulating biological tissue using low-intensity light energy to stimulate acupuncture points are disclosed in U.S. Pat. Nos. 6,013,096, 6,238,424; 6,063,1089; 6,471,716; and 6,074,411(Lai et al.), which describes multi-diodes, self-adhesive using holder to attach diode modules onto patient's body. However, Lai's design can produce inaccuracy in terms of the thickness changes to the actual depth of acupuncture points. Furthermore, by placing a diode laser module into a counterbored hole in a holder, that device has difficulty maintaining an exact illumination 90° angle because the holder is made of soft, plastic foam paper.

For ideal biological tissue stimulation, a combination of wavelengths must be used to achieve illumination to specific depths at acupuncture points and to stimulate several tissue layers to the specific depths simultaneously. A third LED is added to the wand to produce therapeutic heat as moxibustion in TCM of specific light color of color therapy principles. Plural probes and wands provide the ability to treat a number of symptoms by simultaneously stimulating a plurality of acupuncture points. The probes and wands are made self-adhesive with a double-sided, non-allergenic tape to avoid the inconvenience of hand-held models (with which inconsistent radiation can result from movements of the practitioner/patient during treatment). The apparatus also saves time by treating more than one area at once.

A benefit of the present invention is that if the depth of an acupuncture point is variable, a practitioner can set a specific depth of each point in controlling software, providing more accurate treatment at that point's location. A fixed preset illumination depth (for example 3 cm depth, as in the Lai design) is not correct for all acupuncture points. For example, a hand acupuncture point is much closer to the surface than an acupuncture point located at the thigh of a patient.

Whereas prior devices required one to set a single time for all treatments, the present invention provides for variable treatment times. To fulfill the principles of TCM, the practitioner needs to stimulate each TCM acupuncture point by one of the following choices: tonify, sedate or even method. The present invention is built to control the frequency, intensity, dosage, and pulsing of light to satisfy these principle requirements. Pulsing the emissions not only affects the stimulation/inhibition of the biological tissue reaction; it also increases the life span of the treatment unit compared to continuously emitting models.

Taking the incident radiation and angle of reflection into account, the exact location of acupuncture point will be somewhat relative only. So another object of this invention is to minimize human errors in the complicated setting of depths (depending on area), frequencies, intensities, and dosages.

An apparatus according to this invention is an automated system, like a small computer, with specific operating software. Practitioners need only select a certain part or treatment area of the body; then the software automatically sets the frequency, intensity, and dosage and memorizes the settings for the next time. While the automatic mode is particularly convenient for the practitioner, the invention also provides an optional manual mode, allowing for more flexibility in treatment.

An important advantage is that the probes and wands may be started and stopped at the same time, so that they stimulate the body simultaneously to create an ideal effect, considering that the human body is an integrated system.

The invention combines techniques and methods from several different areas of medicine into an inventive treatment method. It also enables one to apply acupuncture and moxibustion to regulate Qi in TCM, or Prana in Ayurvedic, or vital life force of Hippocrates, without using metal needles or burning wools.

One can stimulate the production of certain hormones and enzymes, without the complication of injecting synthesized materials, by placing the plural probes and wands at specific glands' anatomical location to affect the endocrine system. By using LEDs of five different colors (such as white, blue, green, red, and yellow), one can perform color therapy. According to the TCM, these colors correspond to the five elements of the world. Red and infrared diodes are absorbed by the skin, muscles, tissues, and bones and work at the cellular level. The color red represents the element fire, or the cardiovascular system. Yellow represents the element earth, and provides a neutral/central balance state of the body, as related to the stomach. The yellow lights can be a great stimulant for the nervous system as well as toning muscles (spleen dominates muscle according to TCM). White represents the metal element and transformation of the body system that relates to your lung system, especially allergies. Blue represents the water element that relates to the kidney and your willpower; it is best for calming and gives a relaxing effect on treatment therapy. Green represents the wood element in TCM, which relates to the liver, tendons, and emotional state (stress), harmonizing the bio-electromagnetic energy field that surrounds our body.

Light is bio-energy that moves in a wave pattern. For this reason, the inventive method incorporates sound therapy's wave patterns, which harmonizes the endogenous rhythm of the organs and provides a new generation of therapy to enhance the natural building process of biological tissues.

The method and apparatus treat the body with bio-energy light and heat for various conditions. Using this bio-energy light and heat, the apparatus applies energy to patients for the benefits of healing. As modern quantum physics teaches us that all matter is composed of vibrating packets of energy (quanta) that appear to us as particles, so bio-electromagnetic energy is present in all living things with its own specific frequency range, both measurable (frequency of electromagnetic spectrum, such as light (color) and sound) and unmeasurable by conventional scientific methods. We live in a world that is surrounded and affected by the various interconnected magnetic fields of energy. According to Oriental medicine (Ayurvedic and Traditional Chinese Medicine), a human being is a whole, a small universe that is composed of a body, mind, and spirit in a state of harmony including the free flow of invisible vital energy (life force), known as Qi in TCM and Prana in Ayurvedic, throughout the body. Illness is understood to be a result of the disharmonization of energy. BELG medicine aims to restore the harmonious interaction of energy within the patients and their environment by using the inventive bio-energy light and heat device and BELG method. Instead of injecting healthy cellular materials into the body to promote regeneration in cells, BELG method and its devices provide a non invasive stimulation at cellular level without the complication of injection and cell rejection. At the same time, if stimulated at the endocrine system, restoration of the balance of natural hormone/enzymes will be restored without the actual procedure of hormone/enzyme replacement therapy. Through BELG method, energy and light/colored light therapy applies the color principle, which corresponds to the five elements of TCM, including the benefits from the color spectrum.

BELG methods and devices are the perfect answer for oriental medicine. The invention is especially able to regulate and harmonize the vital life force known as Qi in TCM/Prana in Ayurvedic without using a metal needle or burning moxa wool for heat. In other words, energy, light (colored light) and sound therapy are similar because all of them are just different types of wavelengths that generated light beam through the inventive equipment for therapy purposes.

At the same time, neural therapy can be carry out to remove short circuits in the human's electrical network in the absence of anesthetic injection. Another important aspect of BELG method and devices is its ability to incorporate longevity medicine into the practice. By balancing the biochemistry of aging (such as stress hormones/enzymes helicase) as well as enhancing cell functions to boost up immune system, the aging process may be slowed. The invention also relates to the equipment for stimulating mammal tissue with bio-energy light and heat therapy. The equipment has a power source and a central microprocessor that controls twelve other probes and wands to provide bio-energy. The invention works like a small computer with preset protocols for exact frequency, intensity, and time of specific probes/wands to be activated, in order to eliminate human error. Another unique feature is that practitioners are able to select a variety of preset protocols or set their own preferred selections.

SUMMARY OF THE INVENTION

The inventive device provides an apparatus for treating a disorder of a biological tissue in manual by emitting bio-energy light and therapeutic heat having automated selections on time protocol to frequency, intensity, and dosage.

This invention is characterized by the use of different wavelengths combination. For example, one wavelength is applied for penetrating a certain bio-tissue layer while another different wavelength is used for penetrating a deeper layer, and so on. The idea is to combine more than one wavelength to stimulate different bio-tissue simultaneously to achieve a chain reaction through the whole body.

Accordingly, the present invention is directed to a treatment system comprising:

(a) a power source for providing power to a central microprocessor; a central microprocessor running software (which can be updated and monitored from the Internet) having stored time protocols that specify frequency, intensity, and dosage suitable for treating a range of disorders of biological tissue and a means for manually specifying protocols;

(b) a plurality of independent microprocessors to provide individual specific selection, plus paired indicator monitoring lights;

(c) means for a central microprocessor, the control for pulsing the bio-energy light emitting, ranging from 1 to 256 different digital frequencies, intensity, and time interval from 5-30 minutes of each output voltage, of each other 12 individual microprocessors are totally in control and monitored to give the design to stimulation or inhibition of tissue, means of pulsing the bio-energy-emitting gives the life span to the unit longer comparing to a continue emitting model, and preventing the plateau effect of stimulations;

(d) safety means for preventing overexposure;

(e) means for displaying a shut down screen showing probe and wand status at all times including their frequency, intensity, dosage, and time protocol selections, and the remaining time status; and (f) a plurality probes and wands, each adapted to produce light of a wavelength from 360 nm to 1,380 nm, and optionally a second wavelength of from 400 nm to 1,300 nm, including a color LED or SLD.

The apparatus provides light sources of different colors; these correspond to the five elements in TCM for therapeutic purposes. For example, a red diode is best to be absorbed by the skin, muscle, tissues and bone for biochemical reaction at cellular level. A yellow diode provides a harmonized stage of the body. A white diode enhances the immune system which also will fight allergy. A blue diode gives a calming and relaxing effect to the body. A green diode helps control stress. Each optical source may be, for example, a laser, laser diode, a super luminous diode or an LED. Any combination of the various sources can be applied simultaneously. This gives the practitioner the ability to stimulate the biological tissue at different levels, such as the cell membrane, mitochondria, organelle, etc.

Another aspect of the invention relates to a method for stimulating the natural healing process of the biological tissue known as BELG method, which combines key principles from nine different areas of medicines into one. The inventive apparatus is able to regulate Qi and Prana, vital living life force without the complication of metal needles, as in acupuncture.

BELG—the inventive method—stimulates at cellular level to enhance ATP production, protein synthesis, DNA and RNA formation, and many neuro-transmitter in pain control. At the tissue level, better blood circulation; new blood and lymphatic vessels are formed; and collagen is synthesized to assist better wound healing. All these advantages are obtained, without the complexity of gene therapy or hormone/enzyme replacement therapy, by combining different wavelengths, frequency, intensity, and dosages at each treatment location.

The inventive BELG method uses matching wavelengths, as the sounds in Qi Gong therapy have been used, but using wavelengths from 360 nm to 1,380 nm. The treatment protocol, for example, a dose of from 0.5-50 J/cm$^2$, an intensity of from 0.5-6000 W/cm$^2$ and a wavelength from 360 nm to 1380 nm, is set for each treatment location.

The inventive apparatus may be used to treat a wide range of biological tissue dysfunctions or their symptoms, including:

a. Chiropractic medicine—pain management, tissue rehabilitation, nerve irritation, and spinal bone spur.

b. Oriental medicine—regulates Qi and blood for disharmonized body to restore the balance states of the mind, body, and spirit.

c. Pediatric medicine—middle ear infection, toothache, sore throat, cough, running/bleeding nose, indigestion, constipation, and diarrhea.

d. Podiatric medicine—pain management, tissue injuries, nerve irritation, and heel spurs.

e. Substance/chemical dependency—drug addiction, smoking, mood swing, weight management.

f. Internal medicine—immune system enhancement, liver inflammation, liver cirrhosis, hepatitis, diabetes types II, hemorrhoid, benign cyst, small gall bladder/kidney stones, and regulation of secretion of hormones and enzymes.

g. Neurology medicine—semi-paralysis post stroke, spinal cord injuries, nerve irritation, and multiple sclerosis.

h. Dermatological medicine—burns, acne, ulcers of different etiology such as venous ulcer, diabetic ulcer, pressure ulcer, and post traumatic ulcer.

BRIEF DESCRIPTION OF THE DRAWINGS

A more complete appreciation of the present invention and its scope, and the manner in which it achieves the above noted improvements can be obtained by referring to the following detailed description of presently embodiments of the invention taken in connection with the accompanying drawings plus graphs which are briefly summarized below and the claims.

DESCRIPTION OF THE PREFERRED EMBODIMENT

Figure 1:
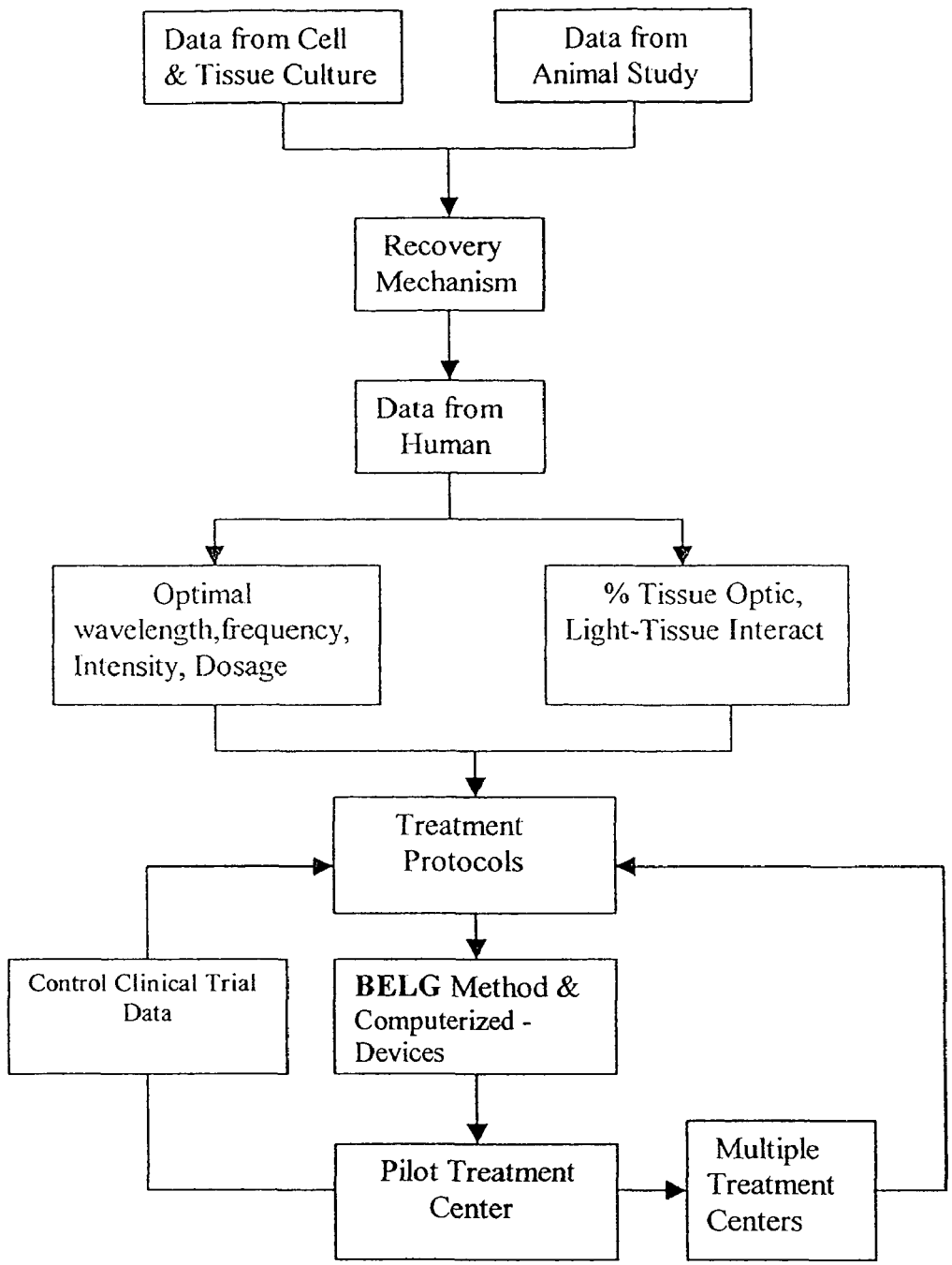
FIG. 1 is a schematic flow chart of the development of BELG treatment method protocols.
Figure 2:
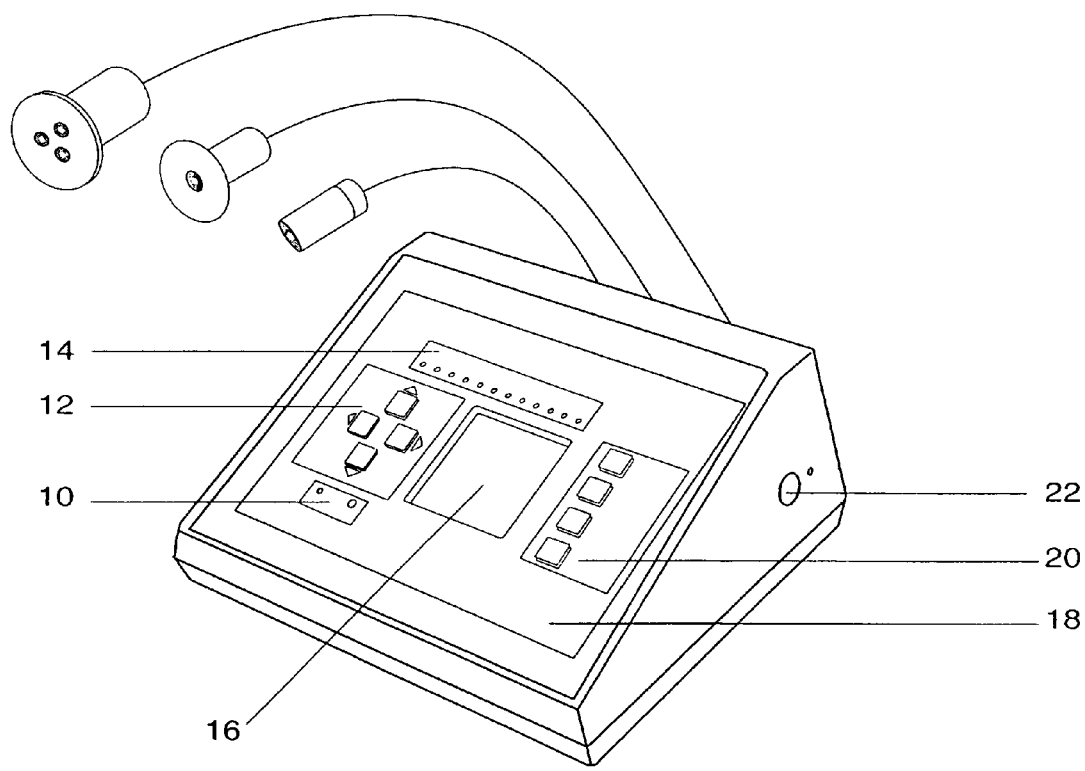
FIG. 2 is a perspective view, from the front, of an apparatus embodying my invention.
Figure 3:
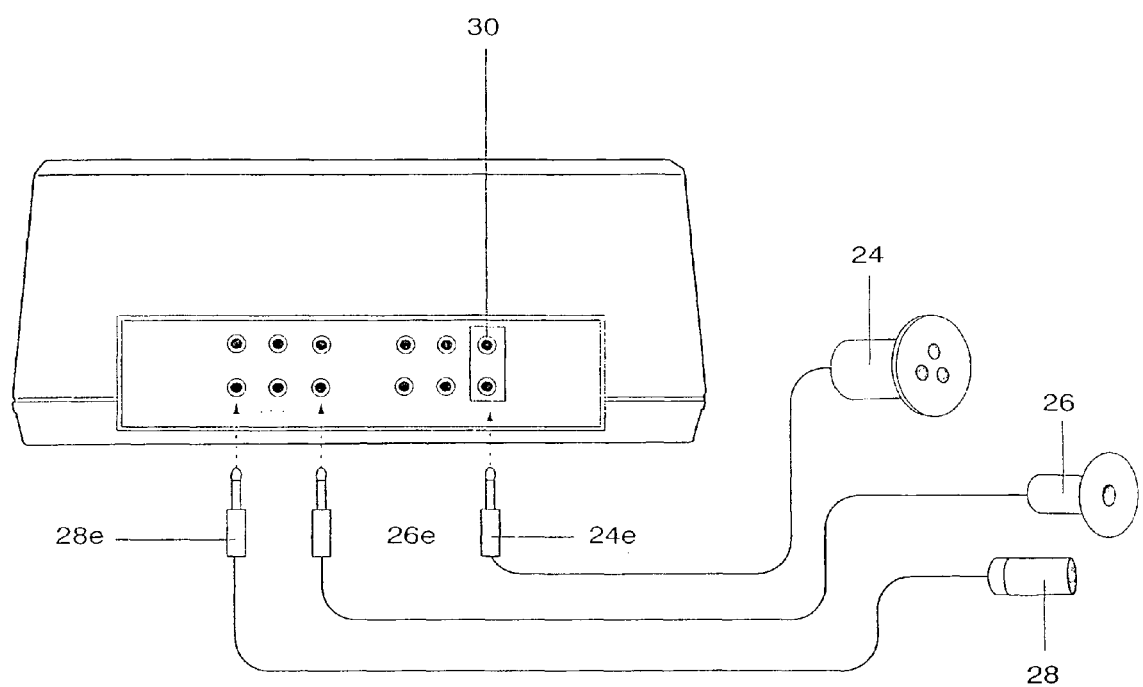
FIG. 3 is a rear elevation of the apparatus.
Figure 4:
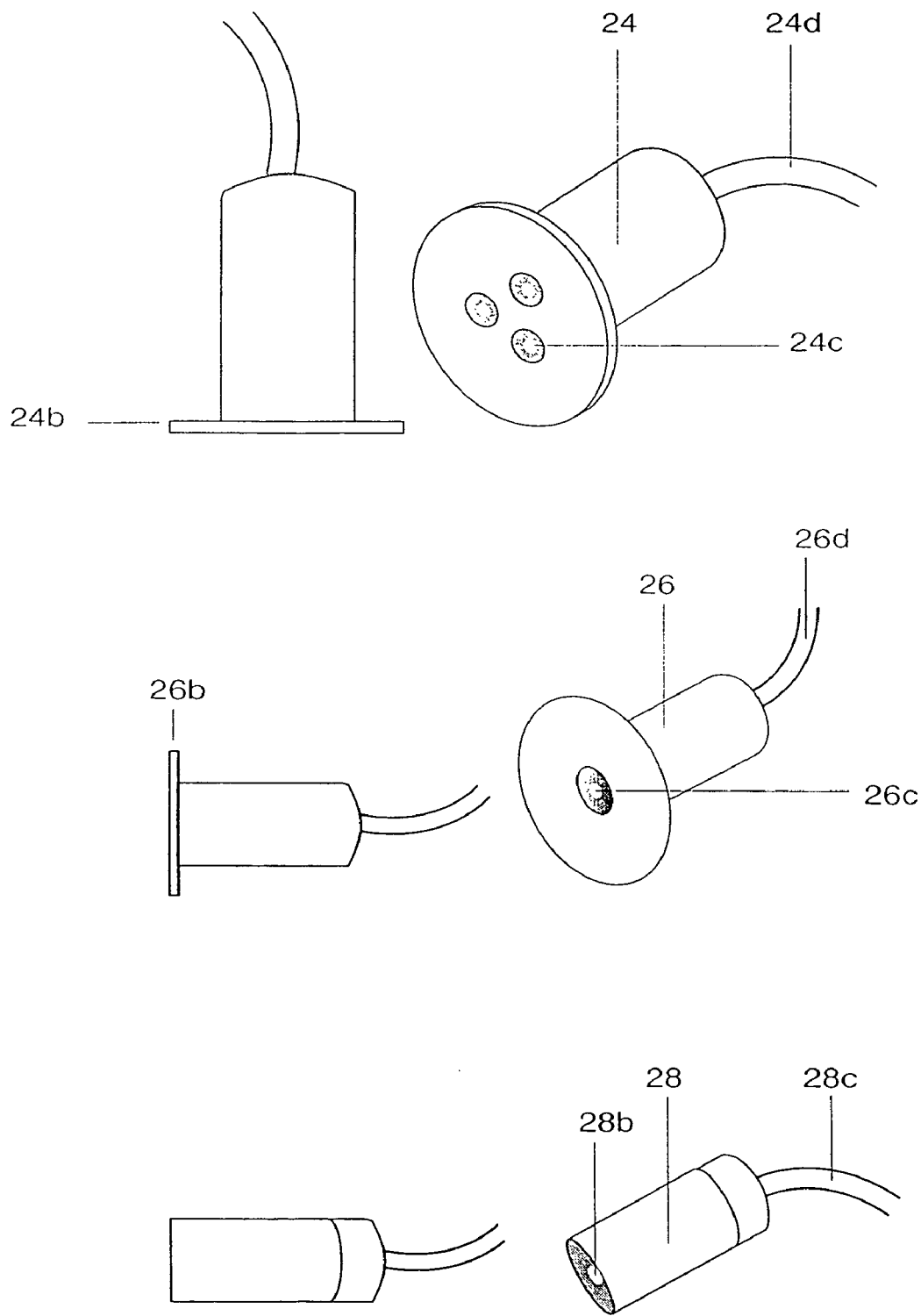
FIG. 4 shows a wand, probe, and ear probe according to the invention.
Figure 5:
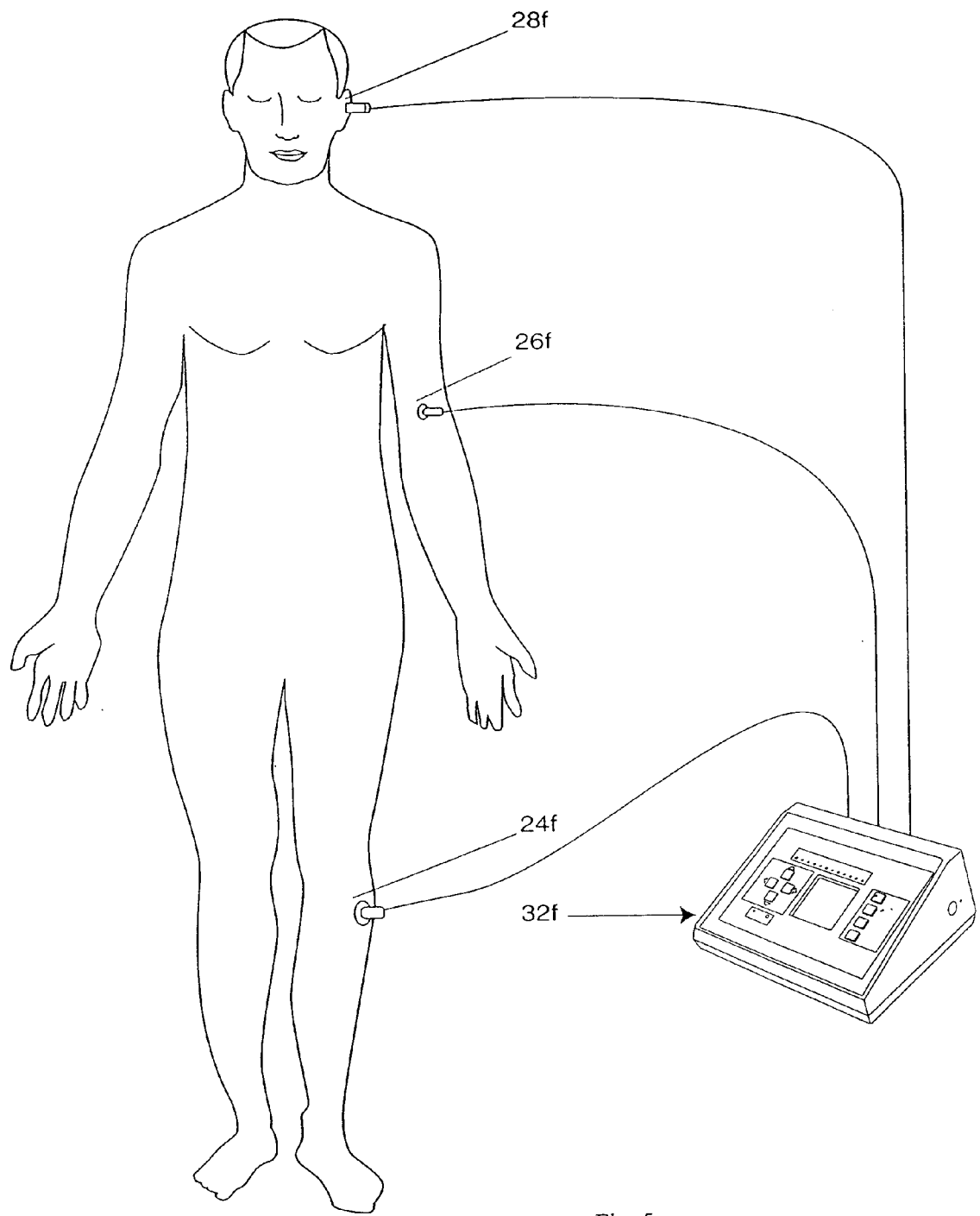
FIG. 5. shows the locations for placing wands and probes along the umbilicus for diabetes type II condition.

A method embodying the invention is illustrated in FIG. 1. Selected treatment protocols may be stored in a base unit 18 (FIG. 2), which has twelve individual microchips. The microchips are controlled by a central microprocessor. The system may be powered by any standard electrical power source. A screen window 16 displays the status of each individual channel: its frequency, intensity, and time. Each of those levels can be adjusted by a set of wands, arrays and probes that can be checked by a phototransistor 10. A count down clock and an audio beeper on the screen 16 signal and automatically turn off light output of all wands and probes at a time set. Each wand, array and probe are independently set, run, and monitored by corresponding red lights 14. There is a flexible treatment protocol for each element; the wands and probes can all be activated simultaneously, or specific selected wands and probes may be run individually. Each of the twelve channels is independently operated and set.

There are a variety of preset treatment protocols from which to choose, each including parameters of frequency, pulse duration, intensity, and time, which can be selected for the optimal dosage to treat a particular disorder. The clinically proven treatment dosage is set in a data bank by the software, as indicated in Table 1.

TABLE 1

| Area | Depth (mm) | Frequency | Intensity | Duration (min.) |
| --- | --- | --- | --- | --- |
| Arm (upper) | 10-15 | 6-7-8-9 | 8, 9 | 25 |
| Back | 10-20 | 6-7 | 8, 9, 10 | 30 |
| Buttock | 10-50 | 4-5-6-7 | 9, 10 | 30 |
| Chest, Abdomen | 5-10 | 7-8 | 8, 9 | 25 |
| Ear | 2 | 9 | 7, 8 | 20 |
| Face | 6-1.2 | 6-7-8 | 7, 8 | 20 |
| Finger | 2-4 | 9 | 8, 9 | 20 |
| Foot | 2-4 | 8-9 | 8, 9, 10 | 30 |
| Forearm | 3-15 | 6-7-8 | 8, 9 | 25 |
| Hand | 3-10 | 7-8 | 8, 9 | 25 |
| Head | 5-10 | 7-8 | 7, 8 | 20 |
| Leg (lower) | 5-20 | 5-6-7-8 | 8, 9 | 30 |
| Nape | 4-10 | 7-8 | 7, 8 | 20 |
| Neck | 4-8 | 7-8-9 | 7, 8 | 20 |
| Thigh | 10-50 | 3-4-5-6-7 | 9, 10 | 30 |
| Toe | 2-4 | 8-9 | 8, 9, 10 | 30 |

Intensity is the rate of bio-light energy delivery per unit area of bio-tissue/skin, expressed herein in units of milliwatts per square centimeter (mW/cm$^2$). Real intensity on the skin surface depends on light reflection and scattering from the skin and underlying tissue layers.

For applications using non-contact techniques, applied power must be adjusted to compensate for reflection. The reflection coefficient R is 0.4-0.75, depending on wavelength and skin type and condition. Back scattering has to be taken into account for dosimetry as well. In contact technique applications, less power is lost, due to the repeating light reflection back to skin surface from optical source unit. Therefore the required light intensity is different, depending on the technique chosen (contact or non-contact).

The "photo-bio-modulation" phenomenon can be best activated within a certain range of wavelengths. For example, collagen Type 1 production is thought to be affected by bio-energy light in an inverse manner to fibroblast proliferation. When cell proliferation is increased, collagen Type I production is decreased and vice versa (Van Breugel and Bar, 1992, Laser Surg. Med. 12:528-537).

Figure 6A:
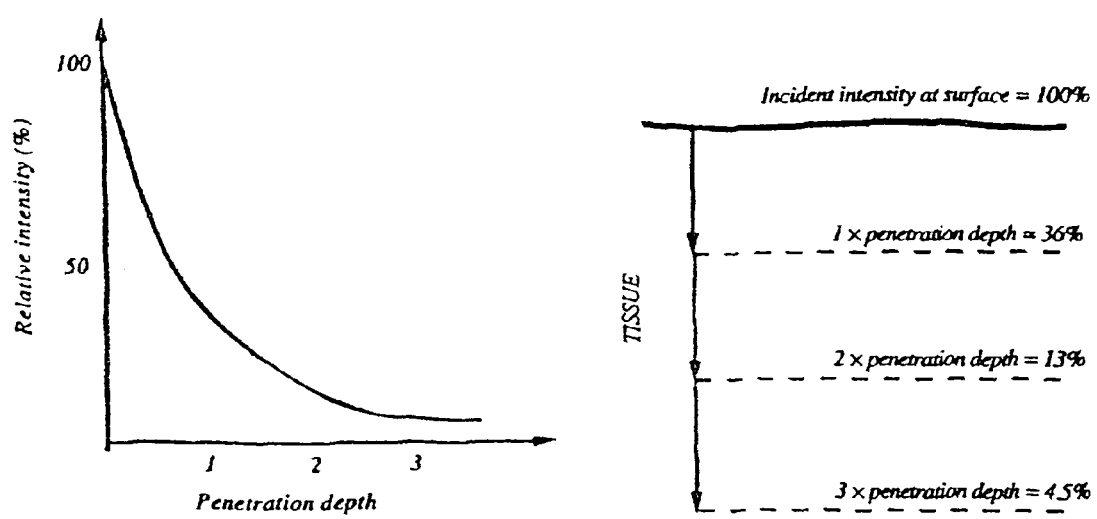
FIG. 6a is a graph showing the Gaussian distribution of the depth of penetration, the exponential attenuation of light radiation intensity within irradiated tissue.
Figure 6B:
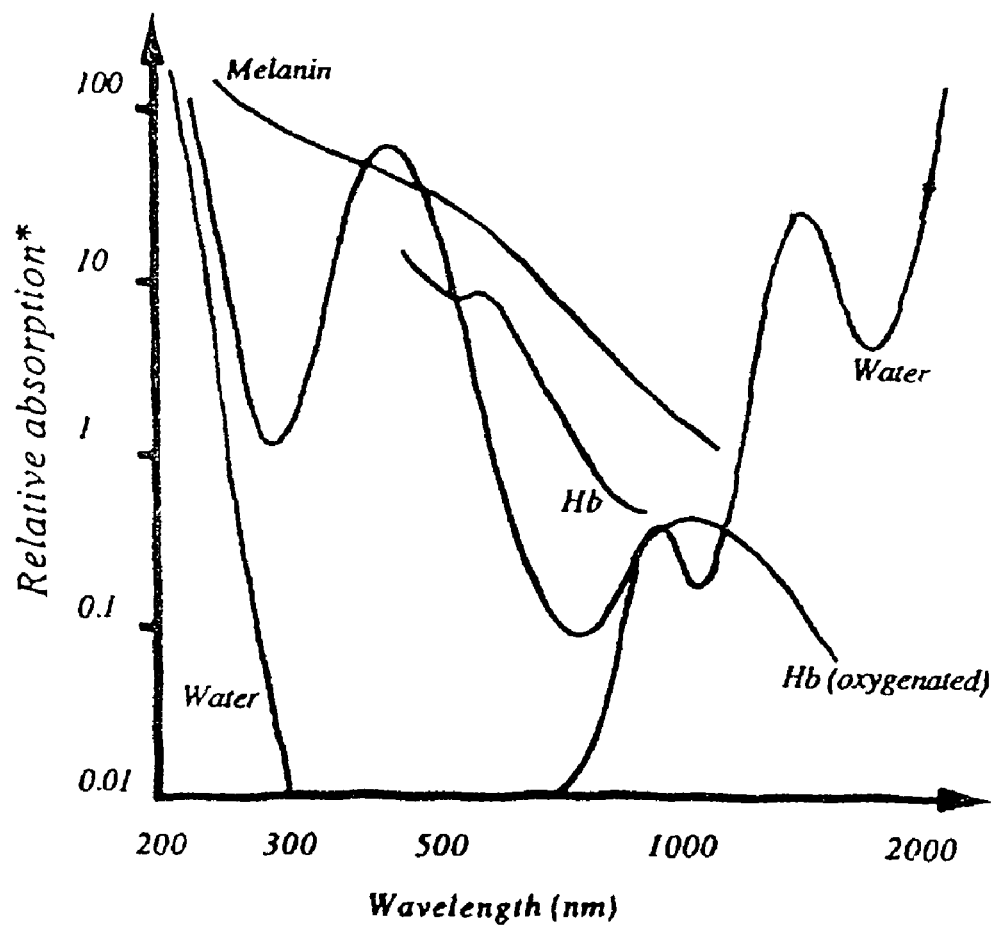
FIG. 6b depicts the approximate absorptions curves for water, oxygenated and reduced haemoglobin, and melanin.

Bio-energy light intensity decreases with depth. In skin and subcutaneous tissue layers, light intensity can be approximately described by Beer's Law, which assumes that the incident light has exponential attenuation (see FIG. 6.1) according to the equation $$I_z = I_{inc} e^{-\gamma z}$$

where:
$I_z$=the irradiance (W/cm$^2$ or mW/cm$^2$) at a given depth,
$I_{inc}$=incident irradiance (W/cm$^2$ or mW/cm$^2$) at the surface of the skin,
z=depth in tissue (cm), and
γ=total attenuation coefficient (cm$^{-1}$)=a+s, where
a=absorption coefficient (cm$^{-1}$) and
s=scattering coefficient (cm$^{-1}$).

The absorption and tissue scattering of photons add to the total amount of light energy within a given volume of tissue, or more correctly, the light fluctuates within the tissue. Light distribution is a relative radiation transfer theory, Mie theory. Thus the light distributions must be looked at in two or three dimensions using the so-called Monte Carlo method (Keijzer et al 1989) which computes a random "walk" for each proton and flow the photon until it is absorbed. Light distribution is then estimated from the distribution of absorbed photons (see FIG. 6.2). Suitable intensities for ideal bio-stimulation are in the range of from 0.1-5000 mW/cm$^2$. For stimulating healing of an ulcer/wound, intensity may preferably be in the range of from 14 to 80 mW/cm$^2$, depending on tissue pathologies. From experiences and clinically proofs, the ideal dosages for treatment are in the range of from 0.1-21 J/cm$^2$; the frequencies are in the range of from 5-200 Hz; and the wavelengths range from 632 nm to 1300 nm, depending on bio-tissue pathologies.

An apparatus for harmonizing energy in Auyverdic therapy with non-ionizing low level bio-energy includes a power source for providing power to light sources which generate bio-energy light beams for healing purposes. The light sources include multiple arrays of both visible and invisible light emitting devices for providing a harmonizing effect on the total energy of the body by balancing all the energy centers of the body.

The light sources preferably have wavelengths in a range of from 530-890 nm, from 900-960 nm, or from 980-1380 nm.

Any of the wavelengths can be turned on or off as needed to treat a specific condition, and preferably, different wavelengths may be selected simultaneously to stimulate different tissue layers for physiological effect.

The apparatus preferably includes means for operating the light source in a repeated pulse mode having a pulse frequency in a range from 5 to 200 Hz.

The bio-energy light parameters are determined automatically by preset protocols defining wavelength, intensity, dosage and treatment values, or manually, as preferred.

A count down clock, controlled by software, may be included which automatically shuts off the apparatus at a preset time.

Patients having high blood pressure were treated with the apparatus described above by the following method:
a) applying light energy with an ear probe to each ear at the auricular helix crust tubercle/liver yang acupuncture point to control blood pressure,
b) if the heart is rate greater than a predetermined high limit, then applying light energy with a probe from 2.0 to 2.5 inches above the wrist crest at the middle of P-6 acupuncture point,
c) determining which of the internal organ(s) is/are the cause for high blood pressure, then applying light energy with respective wands at the particular organ(s),
d) continuing treatment for one week, then if the blood pressure is stable, slowly decreasing the medication dosage to half of the original dosage,
e) repeating steps a-c for the next three weeks, then
f) measuring the blood pressure daily for further evaluation and, if the blood pressure is stable at the normal level, then
g) stopping treatment after a minimum of two months and checking up every one to three months thereafter or, if the blood pressure is not decreased and stable, then
h) continuing treatment by repeating steps a-c.

Patients having diabetes type II were treated by:
a) applying light energy with an ear probe to the mouth area of auricular acupuncture point, a wand at the stomach area of auricular acupuncture point, another wand at the subcortex area of auricular acupuncture point,
b) placing another wand 2.0-2.5 inches lateral to the right side of the umbilicus of the patient and another wand at 135° to the umbilicus and about 2-2.5 inches away,
c) placing a probe 1.5-2.0 inches above the umbilicus, and another probe at 225° to the umbilicus and about 2.0-2.5 inches away,
d) continuing treatment for one week, then
e) measuring the glucose level to check if it is stable and decreased and if so, then
f) reducing medication to half then repeating steps a-d or, if the glucose level is increased or unstable then
g) repeating steps a-d without reducing the medications until the glucose level stays stable and
h) continuing the treatment for one to three months.

Semi-paralyzed patients were treated post-stroke with a method which included steps of:
placing the applicators at acupuncture points corresponding to observed symptoms,
placing a wand of mixed wavelengths at the elbow joint-anterior aspect of LI-11 acupuncture point and at the knee joint of the posterior side of UB-40 acupuncture point on a problem side,
placing an ear probe one on each ear at the auricular helix crus tubercle/liver yang point of acupuncture to control blood pressure,
placing other probes as follows:
a first probe at the shoulder mid point of the joint of LI-15 acupuncture point,
a second probe at the deltoid muscle end, 3-3.5 inches below the top of the shoulder joint, of the LI-14 acupuncture point,
a third probe at the 1-1.5 inches away from the web of the thumb and index fingers, of LI-4 acupuncture point,
a fourth probe at the lateral anterior ⅓ from the tail bone on the buttock, of GB-30 acupuncture point,
a fifth probe at the sagital midline of the body about at the tip of the middle finger when lying next to the body, of GB-31 acupuncture point,
a sixth probe 3.0-3.5 inches below the knee crest line on the lateral side of the lower leg, of GB-34 acupuncture point,
a seventh probe one inch next to the ankle on the lateral side, of UB-60 acupuncture point,
an eighth probe 1.0-1.5 inches away from the web of the big toe and the second toe, at Liv-3 acupuncture point, placing the probes and wands at corresponding nerve roots as to the symptoms, bilaterally alone the spinal process and other areas, placing the probes and wands along the Trigeminal nerve (CN III) said facial deviation on the opposite side of the problem side, placing the first probe at the temple, of taiyang acupuncture point, placing two wands about 2.0-2.5 inches laterally from the umbilicus for digestion symptoms, and placing two wands between L2-L4 on the back about one inch from the spine for kidney symptoms.

Numerous subjects having various conditions were treated with light according to this invention. The subjects' recoveries were evaluated, the results appearing in Table 2.

TABLE 2

Figure 7A:
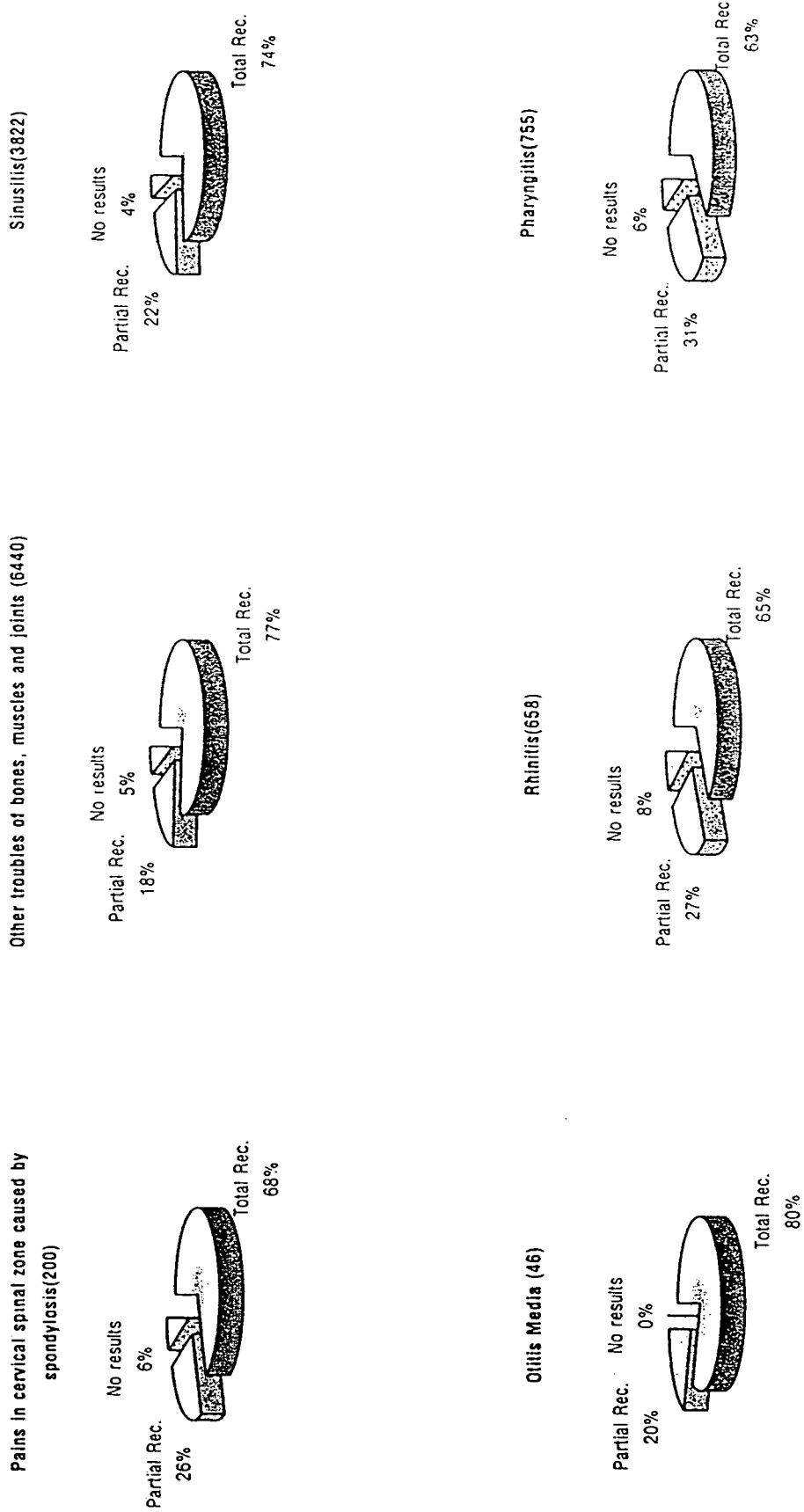
FIGS. 7a-7c graphically illustrate recovery statistics.
Figure 7B:
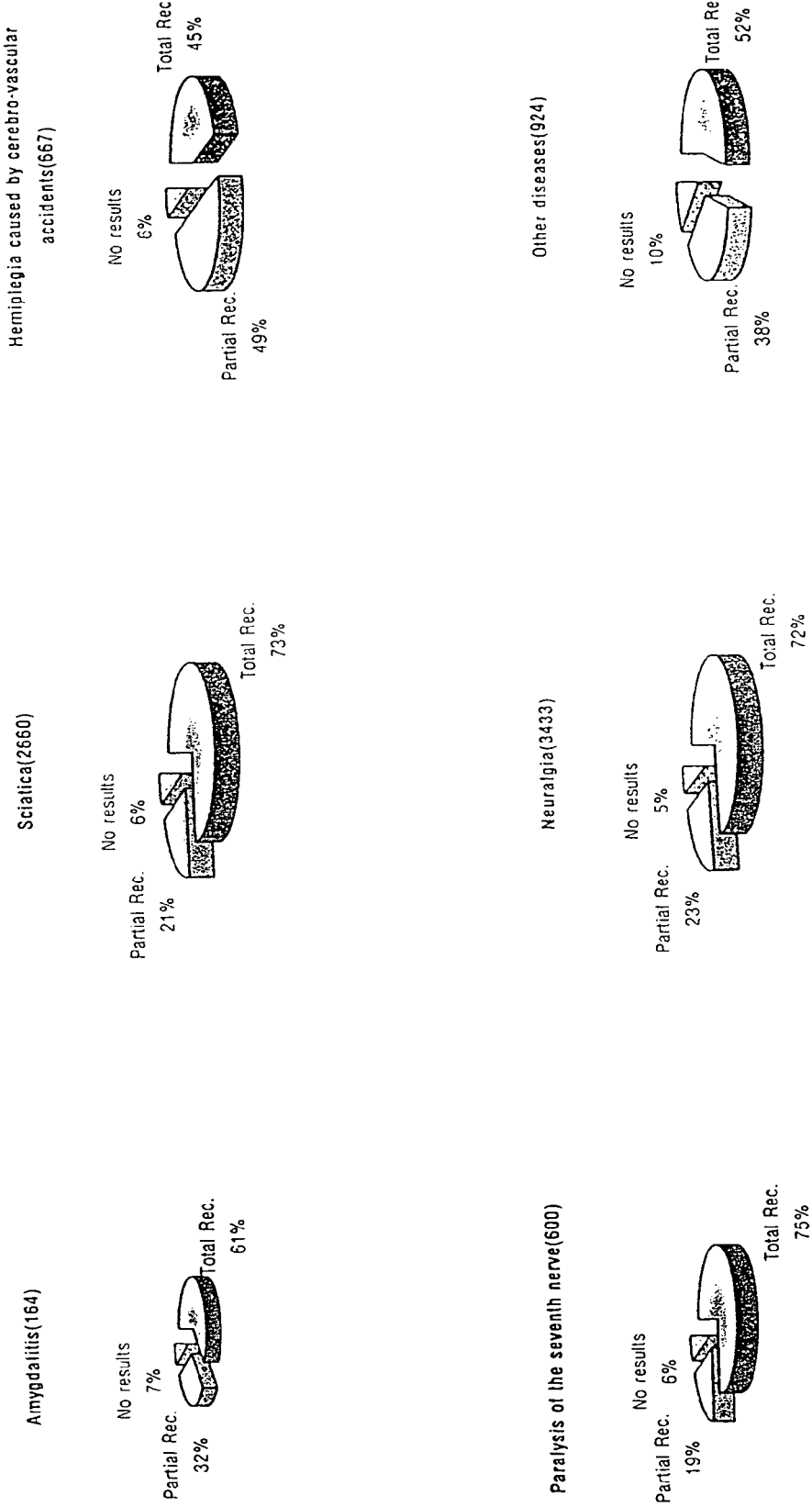
Figure 7C:
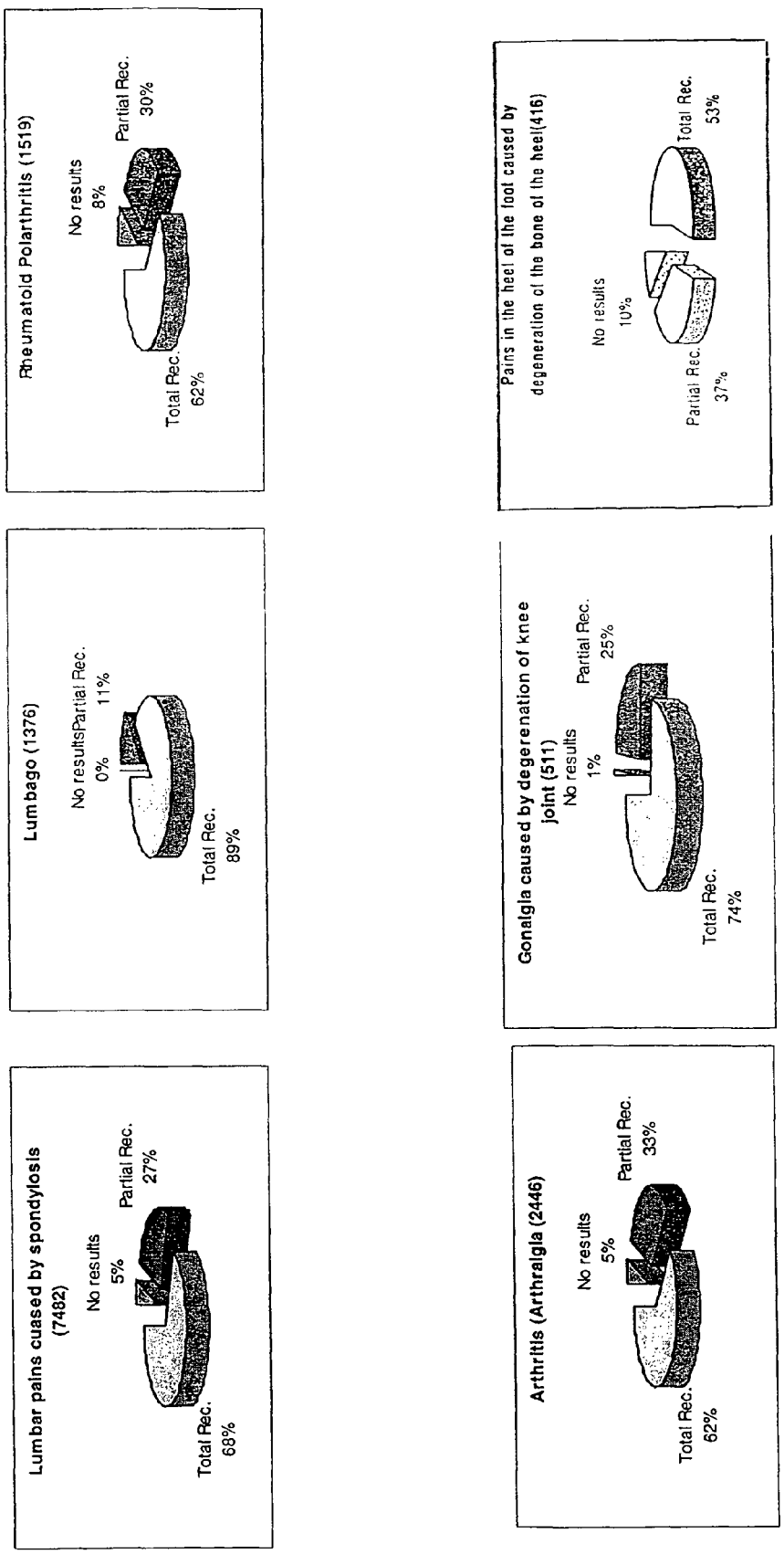

| Troubles and diseases treated | Number of cases | Total Recovery | Partial Recovery | No Results | Percentage of Total and Partial Recovery |
|---|---|---|---|---|---|
| Lumbar pains caused by spondylosis | 7482 | 5086 (67.98%) | 1998 (26.70%) | 398 (5.32%) | 94.68% |
| Lumbago | 1376 | 1221 (88.74%) | 149 (10.83%) | 6 (0.44%) | 99.56% |
| Rheumatoid polyarthritis | 1519 | 938 (61.75%) | 452 (29.76%) | 129 (8.49%) | 91.51% |
| Arthritis - Arthralgia | 2446 | 1502 (61.41%) | 814 (33.28%) | 130 (5.31%) | 94.69% |
| Gonalgia caused by degeneration of knee joint | 511 | 379 (74.17%) | 127 (24.85%) | 5 (0.98%) | 99.02% |
| Pains in the heel of the foot caused by degeneration of the bone of heel | 416 | 219 (52.64%) | 155 (37.26%) | 42 (10.10%) | 89.90% |
| Pains in the cervical spinal zone caused by spondylosis | 200 | 137 (68.50%) | 51 (25.50%) | 12 (6.00%) | 94.00% |
| Other troubles of bones, muscles | 6440 | 4923 (76.44%) | 1177 (18.28%) | 340 (5.28%) | 94.72% |
| Sinusitis | 3822 | 2826 (73.94%) | 828 (21.66%) | 168 (4.40%) | 95.60% |
| Otitis media | 46 | 37 (80.43%) | 9 (19.57%) | 0 (0.00%) | 100.00% |
| Rhinitis | 658 | 431 (65.50%) | 177 (26.90%) | 50 (7.60%) | 92.40% |
| Pharyngitis | 755 | 475 (62.91%) | 233 (30.86%) | 47 (6.23%) | 93.77% |
| Amygdalitis | 164 | 100 (60.98%) | 53 (32.32%) | 11 (6.71%) | 93.29% |
| Sciatica | 2660 | 1955 (73.50%) | 557 (20.94%) | 148 (5.56%) | 94.44% |
| Hemiplegia caused by cerebro-vascular accidents | 667 | 298 (44.68%) | 332 (49.78%) | 37 (5.55%) | 94.45% |
| Paralysis of the seventh nerve | 600 | 450 (75.00%) | 116 (19.33%) | 34 (5.67%) | 94.33% |
| Neuralgia | 3433 | 2491 (72.56%) | 773 (22.52%) | 169 (4.92%) | 95.08% |
| Other diseases | 924 | 483 (52.27%) | 349 (37.77%) | 92 (9.96%) | 90.04% |
| Total number of cases | 34119 | 23951 (70.20%) | 8350 (24.47%) | 1818 (5.33%) | 94.67% | placing the wand 0.5 inch laterally from the corner of the lip of St-4 acupuncture point, placing the second probe at the jaw angle of ST-7 acupuncture point, placing the third probe 0.5-1.0 inch below the lip at midline of REN-24 acupuncture point, placing three probes 0.5 inch apart laterally along C4-C6 on the problem side of the spinal process for arm/finger problems and/or placing five probes 0.5 inch apart laterally along T8-T12 for digestion and stress problem and/or placing five probes 0.5 inch apart laterally along L2-S2 for leg/urination/defecation problem, placing probes and wands at corresponding organ anatomological locations corresponding to the symptoms, placing two wands about two inches apart at the liver area, just below the rib cage on the right hand side of the patient for liver symptom, The tabular data is illustrated graphically in FIGS. 7a-7c.

Since the invention is subject to modifications and variations, it is intended that the foregoing description and the accompanying drawings shall be interpreted as only illustrative of the invention defined by the following claims.

We claim:

1. An apparatus for harmonizing energy in Auyverdic therapy with non-ionizing low level bio-energy, said apparatus comprising:
    a plurality of light sources which generate light beams of different wavelengths for healing purposes,
    a power source for providing power to said light sources,
    said light sources being arranged in multiple independently operable arrays of both visible light emitting devices and invisible light emitting devices for providing a harmonizing effect on the body by balancing all the energy centers of the body, and
    a central microprocessor for controlling operation of said light sources, wherein said light sources are operated simultaneously to penetrate different bio-tissue layers, and wherein each of said light source arrays is controlled automatically by said central microprocessor according to a respective one of plural preset protocols, each said protocol defining wavelength, intensity, dosage and treatment values suitable for treatment of a different condition or part of the body.

2. The apparatus of claim 1, further including a plurality of different applicators including probes, ear probes, wands and arrays to provide non-ionizing bio-energy for treatment.

3. The apparatus of claim 2, wherein the applicators can be turned on or off as needed during treatment.

4. The apparatus of claim 2, wherein the applicators are made of a plastic material having low thermal and electrical conductivity.

5. The apparatus of claim 1, further comprising software adapted to control a count down clock which automatically shuts off the apparatus at a preset time.

* * * * *